Sept. 6, 1949. C. A. CHASE Plant Pat. 870
HYBRID TEA ROSE PLANT
Filed Aug. 20, 1947
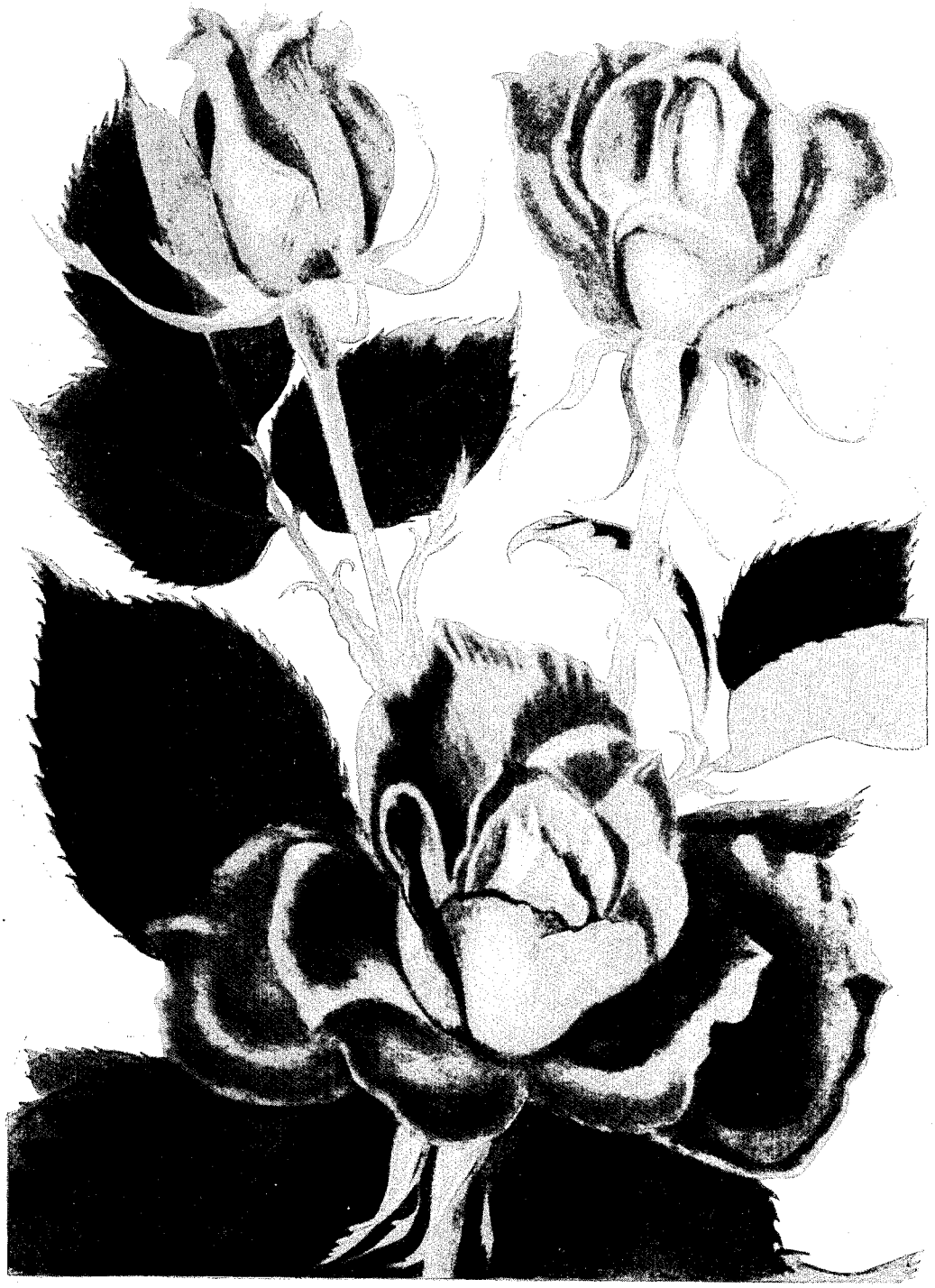
Clarence A. Chase, INVENTOR
By Orville M. Kile, Plant Pat. Agt.

Patented Sept. 6, 1949

Plant Pat. 870

UNITED STATES PATENT OFFICE

870

HYBRID TEA ROSE PLANT

Clarence A. Chase, Eugene, Oreg., assignor to Chase Gardens, Eugene, Oreg., a partnership.

Application August 20, 1947, Serial No. 769,729

1 Claim. (Cl. 47—61)

My present discovery relates to improvements in hybrid tea rose plants with particular reference to the type used for greenhouse culture.

The new variety originated at our greenhouses in Oregon as a sport of Better Times, and is like its parent in many respects. The principal differences lie in the vigor of growth, size and color of foliage, and character of the blooms. Asexual reproduction of the new variety has shown its qualities to be permanent.

Accompanying illustrations show three typical specimens of the flower of my new variety in various stages of opening, together with portions of the stems and foliage. These illustrations were made in July from flowers grown in our greenhouses, and all appear in as nearly natural colors as it is possible for the artist to make them. Allowances must be made, however, for variations between specimens and in different seasons and growing conditions.

Following is a detailed description of my new variety. Color plate references indicate Ridgway's Color Standards and Nomenclature. Where plate references are not given, the ordinary dictionary meaning of the term is intended.

*The plant*

Growth and form: This variety is extremely vigorous and healthy. It is a tall upright bush.

Propagation: Easy.

Blooming habit: Continuous, producing an average number of flowers but all of very high quality.

Stems: Stiff and very strong. A few light brown thorns are found on the stems and these are medium in size and slightly downward-pointing.

Foliage:

*Type.*—3 to 5 leaflets.

*Quantity.*—Abundant.

*Size.*—Very large, terminal leaflet averaging 2½ by 4 to 4½ inches, the entire leaf with its stem measuring about 7 inches in length.

*Shape.*—Ovate with acuminate apex. Edge sharply and deeply serrate.

*Texture.*—Smooth and substantial.

*Color.*—Very dark, varying from Yew Green (Plate XXXI) to Empire Green (Plate XXXII) on the upper surface. Under surface is much lighter and sometimes bronzed. Rachis is usually reddish brown and the veinings sometimes show this color also.

*Stipules.*—Long, narrow, and sharp-pointed.

*The flower*

Bud:

*Form.*—Long, but not particularly pointed.

*Size.*—Large, measuring 2 inches in length just before beginning to unfold. This is considerably larger than the bud of its parent.

*Opening.*—Slow, with petals reflexing only slightly at edges.

*Color.*—Dark red, approximately Carmine (Plate I).

*Peduncle.*—Very strong and upright. Medium in length. Approximately Grass Green (Plate VI).

*Calyx and sepals.*—Reflex early. Slightly foliaceous. Edges almost smooth. Color about like peduncle on outside of calyx with tips and inner surface frequently tinged with reddish brown. Inside surface slightly pubescent.

Bloom:

*Size.*—Large, opening to about 5½ inches in diameter. This great size is due both to the large size of the petals and to their heavy texture.

*Form.*—Full, high-centered. Opens loosely but retains high center.

*Petalage.*—Usually has 34 to 46 petals, varying somewhat with the season.

*Aspect.*—Silky on under surface of petal, but very velvety on the upper surface. This velvety aspect is retained until the flower is old.

*Fragrance.*—Light and pleasing fragrance which holds well.

*Color.*—The general color effect is a rich dark red, approximately Carmine (Plate I), with slightly lighter center. The color is very lively and does not turn bluish with age.

Petals:

*Size.*—Outer petals are very large, measuring approximately 2½ inches in each direction.

*Shape.*—Ovoid with definite point at tip. Edges slightly wavy. Reflex only slightly.

*Aspect.*—Very velvety on upper surface. Silky on under surface.

*Texture.*—Substantial but not coarse.

*Color.*—Outer petals have rich dark red tips, toning down to something like cerise at their base. The central petals are considerably lighter tones of the same general colors.

Longevity of bloom: Lasts well.

Reproductive organs:

*Pistils.*—Many, bunched.

*Stamens.*—Many, surrounding pistils. *Filaments* red; *anthers* gold.

*Comparison*

The principal differences between my new variety and its parent, Better Times, are as follows:

1. My variety has a much more vigorous type of growth.
2. My variety has much darker foliage.
3. My variety has much larger foliage.
4. The flower of my variety has petals which are a little heavier in texture.
5. The flower of my variety is slightly larger, due partially to the fact that the petals are of heavier texture.
6. The flower of my variety is much darker and a truer red.

7. The flower of my variety does not turn blue with age as does the flower of Better Times.
8. The flower of my variety is more pointed in form.
9. The bud of my variety is larger.
10. The flower of my variety is more velvety.

Having thus disclosed my discovery, I claim:

The new and distinct variety of hybrid tea rose plant, substantially as herein disclosed, characterized particularly by its vigorous growth; its strong stiff stems and peduncle; its very large and dark foliage of heavy substance; the large size of its bud; and the production of good quality blooms combining large size, full petalage, substantial texture, high-centered loose form, velvety aspect, and rich dark red color which does not blue with age.

CLARENCE A. CHASE.

No references cited.